US011000458B2

(12) United States Patent
Maczkiewitz et al.

(10) Patent No.: US 11,000,458 B2
(45) Date of Patent: May 11, 2021

(54) METHOD AND PRODUCT FOR PRODUCING FORMULATIONS CONTAINING CERAMIDE

(71) Applicant: Evonik Operations GmbH, Essen (DE)

(72) Inventors: Ursula Maczkiewitz, Essen (DE); Maria Mecking, Bottrop (DE); Annika Schrader, Bremen (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/491,685

(22) PCT Filed: Mar. 12, 2018

(86) PCT No.: PCT/EP2018/056032
§ 371 (c)(1),
(2) Date: Oct. 4, 2019

(87) PCT Pub. No.: WO2018/177730
PCT Pub. Date: Oct. 4, 2018

(65) Prior Publication Data
US 2020/0246228 A1 Aug. 6, 2020

(30) Foreign Application Priority Data
Mar. 27, 2017 (EP) .................................... 17163002

(51) Int. Cl.
| | |
|---|---|
| *A61K 8/06* | (2006.01) |
| *A61K 8/02* | (2006.01) |
| *A61K 8/31* | (2006.01) |
| *A61K 8/34* | (2006.01) |
| *A61K 8/36* | (2006.01) |
| *A61K 8/37* | (2006.01) |
| *A61K 8/68* | (2006.01) |
| *A61K 8/92* | (2006.01) |
| *A61Q 19/00* | (2006.01) |

(52) U.S. Cl.
CPC ............ *A61K 8/062* (2013.01); *A61K 8/0216* (2013.01); *A61K 8/31* (2013.01); *A61K 8/342* (2013.01); *A61K 8/361* (2013.01); *A61K 8/375* (2013.01); *A61K 8/68* (2013.01); *A61K 8/922* (2013.01); *A61K 8/925* (2013.01); *A61Q 19/00* (2013.01); *A61K 2800/10* (2013.01); *A61K 2800/805* (2013.01)

(58) Field of Classification Search
CPC ........ A61K 8/062; A61K 8/0216; A61K 8/31; A61K 8/342; A61K 8/361; A61K 8/375; A61K 8/68; A61K 8/922; A61K 8/925; A61K 2800/10; A61K 2800/805; A61Q 19/00

See application file for complete search history.

(56) References Cited

U.S. PATENT DOCUMENTS

| | | | |
|---|---|---|---|
| 5,610,040 A | 3/1997 | Smeets et al. | |
| 5,631,356 A | 5/1997 | Smeets et al. | |
| 5,693,677 A | 12/1997 | Lambers et al. | |
| 5,792,794 A | 8/1998 | Lambers et al. | |
| 5,840,940 A | 11/1998 | De Pater et al. | |
| 5,910,425 A | 6/1999 | De Boer et al. | |
| 5,919,960 A | 7/1999 | Weber et al. | |
| 6,001,375 A | 12/1999 | Lambers et al. | |
| 6,054,599 A | 4/2000 | Weber et al. | |
| 6,117,433 A | 9/2000 | Edens et al. | |
| 6,204,006 B1 | 3/2001 | De Boer et al. | |
| 6,420,604 B1 | 7/2002 | Weber et al. | |
| 6,852,892 B2 | 2/2005 | Van Boom et al. | |
| 7,090,860 B2 * | 8/2006 | Yousfi ...................... | A61K 8/02 424/401 |
| 7,148,260 B2 | 12/2006 | Dietz | |
| 7,597,899 B2 | 10/2009 | Lambers et al. | |
| 8,088,399 B2 | 1/2012 | De Lacharriere et al. | |
| 8,372,595 B2 | 2/2013 | Schaffer et al. | |
| 8,647,848 B2 | 2/2014 | Hollmann et al. | |
| 9,234,222 B2 | 1/2016 | Van Den Berg et al. | |
| 9,388,439 B2 | 7/2016 | Schaffer et al. | |
| 9,404,118 B2 | 8/2016 | Köhler et al. | |
| 9,598,711 B2 | 3/2017 | Köhler et al. | |
| 2003/0064936 A1 | 4/2003 | Nieuwenhuizen et al. | |
| 2004/0005282 A1 | 1/2004 | Gaetani et al. | |
| 2007/0122871 A1 | 5/2007 | Van Den Berg et al. | |

(Continued)

FOREIGN PATENT DOCUMENTS

| | | |
|---|---|---|
| DE | 10 2009 001710 A1 | 9/2010 |
| EP | 0 797 976 A2 | 10/1997 |

(Continued)

OTHER PUBLICATIONS

Craframo LabSolutions (2016).*
Eckstein et al., U.S. Appl. No. 16/355,981, filed Mar. 18, 2019.
German language International Search Report dated May 30, 2018 in PCT/EP2018/056032 (5 pages).
German language Written Opinion dated May 30, 2018 in PCT/EP2018/056032 (7 pages).
International Search Report dated May 30, 2018 in PCT/EP2018/056032 (3 pages).
Lee et al., "Bio-inspired phase change materaisl designed for high specific heat of solid phase," copyright Jul. 2014, Thermochimica Acta, Elsevier Science Publishers, Amsterdam, NL, vol. 591, pp. 61-67 (3 pages).

(Continued)

*Primary Examiner* — Shirley V Gembeh
(74) *Attorney, Agent, or Firm* — Taylor English Duma LLP; Philip P. McCann

(57) ABSTRACT

The subject matter of the invention is a method for producing a formulation containing ceramide, comprising the method steps:
A) Melting a mixture containing at least one wax and at least one ceramide,
B) Cooling the melted mixture to obtain a solidified melt containing the at least one wax and the at least one ceramide,
C) Incorporating the solidified melt into a formulation containing oil.
The invention also relates to the solidified melt of the aforementioned mixture.

17 Claims, No Drawings

(56) References Cited

U.S. PATENT DOCUMENTS

| | | |
|---|---|---|
| 2007/0264716 A1 | 11/2007 | Boergel et al. |
| 2011/0065801 A1 | 3/2011 | Hollmann et al. |
| 2011/0165203 A1* | 7/2011 | Bouwstra ............... A61K 47/44 424/400 |
| 2013/0330427 A1* | 12/2013 | Smigel .................... A61K 8/68 424/725 |

FOREIGN PATENT DOCUMENTS

| | | |
|---|---|---|
| EP | 1 426 401 A1 | 6/2004 |
| EP | 1 955 692 A1 | 8/2008 |
| FR | 2 759 902 A1 | 8/1998 |
| JP | 2008297301 A | 12/2008 |
| WO | 1998053797 A1 | 12/1998 |
| WO | 1999029293 A1 | 6/1999 |
| WO | 2002/060405 A1 | 8/2002 |
| WO | 2002/060406 A1 | 8/2002 |
| WO | 2011/114214 A2 | 9/2011 |

OTHER PUBLICATIONS

Lambers et al., U.S. Appl. No. 08/564,228, filed Dec. 6, 1995 (abandoned).

Roobol et al., U.S. Appl. No. 09/720,077, filed Aug. 31, 2001 (abandoned).

* cited by examiner

METHOD AND PRODUCT FOR PRODUCING FORMULATIONS CONTAINING CERAMIDE

CROSS REFERENCE TO RELATED APPLICATIONS

This application is a 35 U.S.C. § 371 U.S. national phase entry of International Application No. PCT/EP2018/056032 having an international filing date of Mar. 12, 2018, which claims the benefit of European Application No. 17163002.3 filed Mar. 27, 2017, each of which is incorporated herein by reference in its entirety.

BACKGROUND

The invention provides a method for preparing a ceramide-containing formulation comprising the method steps of A) melting a mixture comprising at least one wax and at least one ceramide, B) cooling the molten mixture to obtain a solidified melt comprising the at least one wax and the at least one ceramide, C) incorporating the solidified melt into an oil-containing formulation.

SUMMARY

Ceramides are used in many cosmetic formulations. However, their low solubility and strong tendency to recrystallization complicate the stable incorporation into cosmetic formulations. The prior art addresses this problem by various delivery forms.

For instance, WO1998053797 describes encapsulated water-insoluble active ingredients having amphiphilic character, with a content of water and at least one surfactant from the group of esters of long-chain carboxylic acids with carboxylic acids comprising hydroxyl groups or salts thereof and esters of long-chain carboxylic acids with polyalcohols, in which ceramides may be the water-insoluble active ingredients.

WO1999029293 describes a composition for topical application, comprising a combination of a free sphingoid base and a ceramide.

JP2008297301 describes ceramides and phytosterol derivatives in triglyceride-containing oil solutions in liquid form for incorporation into dermatological preparations.

It was an object of the invention to provide a possibility of incorporating ceramides into formulations, particularly into oil-in-water emulsions, which solves the problems of the prior art described above.

DETAILED DESCRIPTION

Surprisingly, it has been found that the method described hereinafter is able to solve the problem posed by the invention.

The present invention therefore provides a method for preparing a ceramide-containing formulation as described in claim 1.

The invention further provides a solidified melt comprising at least one wax and at least one ceramide.

An advantage of the present invention is that the dissolution temperature for the ceramides in oils is lowered. This makes it possible that ceramide-containing formulations can be prepared in an energy-saving manner since only a relatively small amount of substance has to be heated to high temperatures, and the remaining majority of the formulation constituents can be formulated at relatively low temperatures.

This results in a further advantage, namely that temperature-sensitive ingredients may be incorporated into ceramide-containing formulations.

The high dissolution temperature of the ceramides in oils often presents a technical problem since, for example, sufficiently high temperatures are not attained using steam heaters. This problem is also solved by the invention.

A further advantage of the present invention is that ceramides may also be introduced into formulations in a one-pot process due to the present invention.

Another advantage of the present invention is that the formulations according to the invention have increased storage stability and are thus slower to change in their nature over time, particularly with regard to their viscosity, compared to ceramide-containing formulations according to the prior art.

Another advantage of the present invention is that the formulations according to the invention tolerate a higher number of freeze-thaw steps without significant loss of viscosity, compared to ceramide-containing formulations according to the prior art.

The invention provides a method for preparing a ceramide-containing formulation comprising the method steps of A) melting a mixture comprising at least one wax and at least one ceramide, B) cooling the molten mixture to obtain a solidified melt comprising the at least one wax and the at least one ceramide, C) incorporating the solidified melt into an oil-containing formulation.

In the context of the present invention, the term "wax" is understood to mean substances which are solid at 20° C. and 1 bar and also transparent to opaque but not glass-like and have a melting point of 40° C. or higher at 1 bar.

In the context of the present invention, the term "ceramide" is understood to mean acylated sphingoid bases, where the sphingoid bases are selected from sphingosine, sphinganine, 6-hydroxysphingosine and phytosphingosine.

Unless stated otherwise, all percentages (%) given are percentages by mass.

It is preferable in accordance with the invention if the waxes used in method step A) are cosmetic waxes; these are selected in particular from the group consisting of natural waxes of plant or animal origin, mineral waxes, fats, fatty alcohols, fatty acids, fatty esters, ethers of fatty alcohols, esters of polyethylene oxide and fatty acids, ethers of polyethylene oxide and fatty alcohols and partial glycerol esters.

Preferred natural waxes of plant or animal origin are selected from the group consisting of cotton wax, carnauba wax, candelilla wax, esparto wax, guaruma wax, japan wax, cork wax, montan wax, Ouricury wax, rice germ oil wax, sugarcane wax, beeswax, preen gland fat, wool wax, shellac wax, spermaceti, hydrogenated castor oil and shea butter.

Preferred mineral waxes are selected from the group consisting of microwaxes, ceresin, petrolatum and ozokerite.

Preferred fatty alcohols are selected from the group consisting of saturated fatty alcohols having a carbon chain length of 10 to 22 carbon atoms.

Preferred fatty acids are selected from the group consisting of fatty acids having a carbon chain length of 10 to 22 carbon atoms.

Preferred fatty acid esters are selected from the group of esters of fatty alcohols, esters of glycerol and esters of polyglycerol, esters of polyethylene oxide, esters of sorbitan, esters of sugars such as glucose or sucrose, in particular glyceryl stearate, polyglyceryl-3 methylglucose distearate, polyglyceryl-3 dicitrate/stearate, glyceryl stearate citrate.

It is preferable in accordance with the invention if the ceramide used in method step A) is selected from the group comprising, preferably consisting of, Ceramide NP, Ceramide AP, Ceramide EOP, Ceramide NDS, Ceramide ADS, Ceramide EODS, Ceramide NS, Ceramide AS, Ceramide EOS, Ceramide NH, Ceramide AH and Ceramide EOH, wherein preference is given to Ceramide NP, Ceramide AP, Ceramide EOP, Ceramide NDS, Ceramide ADS, Ceramide EODS, Ceramide NS, Ceramide AS, Ceramide EOS, and wherein particular preference is given to Ceramide NP.

The ratio by weight of wax to ceramide in method step A) and in the solidified melt in method step B) in accordance with the invention is preferably from 50:1 to 1:1, preferably from 20:1 to 2:1, particularly preferably from 9:1 to 4:1.

A preferred method according to the invention is thus characterized in that the mixture in method step A) and the solidified melt in method step B), based on the total mixture and total melt respectively, comprise 70% by weight to 100% by weight, preferably 81% by weight to 99% by weight, particularly preferably 95% by weight to 98% by weight of the at least one wax and the at least one ceramide.

The mixture in method step A) is melted according to the invention preferably at a temperature of 80° C. to 105° C., preferably 85° C. to 99° C., particularly preferably 87° C. to 92° C.

A preferred method according to the invention is thus characterized in that the oil-containing formulation in method step C) is an emulsion, in particular an oil-in-water emulsion, and the method steps comprise C1) heating an oil phase comprising the solidified melt,
C2) heating an aqueous phase
C3) homogenizing the combined oil phase and aqueous phase with each other.

It is preferable in accordance with the invention that in method step C1) and C2), the phases are heated to a temperature of 60° C. to 89° C., preferably 65° C. to 79° C., particularly preferably 69° C. to 76° C.

It is preferred in accordance with the invention that the oil phase is added to the aqueous phase in method step C3), wherein the addition is carried out according to the invention preferably with stirring.

Alternatively, by way of preference in accordance with the invention, the aqueous phase can be added to the oil phase in method step C3), wherein the addition is carried out according to the invention preferably without stirring.

It is advantageous and therefore preferred in accordance with the invention that at least one oil and at least one emulsifier, in particular an oil-in-water emulsifer, are present in the oil phase.

Preferred oils present according to the invention are cosmetic oils. In the context of the present invention, the term "cosmetic oil" is understood to mean liquids (i.e. liquid at 25° C. and 1 bar) immiscible with water which are suitable for preparing cosmetic formulations. In the context of the present invention, immiscible with water signifies that, at room temperature, aqueous mixtures of cosmetic oils at oil concentrations of 0.5-99.5% by volume, based on the total mixture, result in cloudiness visible to the human eye or to the formation of two or more phases. In the context of the present invention, furthermore, cosmetic oils are preferably characterized in that they have an interfacial tension with respect to water of >5 mN/m. Cosmetic oils can be for example oleochemistry- or silicone chemistry-based.

In particular, these are selected from the group of fatty alcohols, esters of linear fatty acids with linear or branched fatty alcohols, esters of branched fatty acids with linear or branched fatty alcohols, esters of linear fatty acids with unbranched or branched polyhydric alcohols, esters of branched fatty acids with unbranched or branched polyhydric alcohols, esters of linear fatty acids with unbranched or branched alcohols, esters of branched fatty acids with unbranched or branched alcohols, esters of alkylhydroxycarboxylic acids with linear or branched fatty alcohols. In addition, mono-, di- or triglycerides in liquid form. In addition, esters of carboxylic acids, aromatic carboxylic acids or dicarboxylic acids with linear or branched fatty alcohols, unbranched or branched polyhydric alcohols or unbranched or branched alcohols. In addition, linear, cyclic or branched hydrocarbons, with or without substituents, with or without double bonds. In addition, vegetable oils, carbonates with unbranched or branched alcohols, carbonates with unbranched or branched polyhydric alcohols, carbonates with linear or branched fatty alcohols. In addition, ethers with or without alkoxy groups, silicone oils with or without organic modification. In addition, mixtures of these oils in any ratios.

By way of preference according to the invention, oil-in-water emulsifiers present in the oil phase are selected from the group consisting of esters of fatty acids with glycerol, polyglycerol, polyethylene oxide, sugars or sorbitan, fatty acid salts, ethoxylated fatty alcohols, ethoxylated fatty acids and ethoxylated silicones.

By way of preference, esters of fatty acids present in the oil phase as oil-in-water emulsifiers are selected from the group consisting of polyglyceryl-3 dicitrate/stearate, polyglyceryl-4 laurate, methylglucose sesquistearate.

By way of preference, ethoxylated fatty alcohols and ethoxylated fatty acids present in the oil phase as oil-in-water emulsifiers are selected from the group consisting of ceteareth-25, ceteareth-15, PEG-40 stearate.

By way of preference, ethoxylated silicones present in the oil phase as oil-in-water emulsifiers are selected from the group consisting of bis-PEG/PPG-20/5 PEG/PPG dimethicone, methoxy PEG/PPG-25/4 dimethicone, bis-PEG/PPG-16/16 PEG/PPG-16/16 dimethicone.

The preferred oil-in-water emulsifier present in the oil phase, with regard to its chemical composition, may optionally be identical to the waxes used according to the invention, but is present in dissolved form at the start of method step C), and can therefore be clearly differentiated from the waxes present in the solidified melt which are present as a solid at this time point.

The ratio by weight of oil phase to aqueous phase in method step C3) in accordance with the invention is preferably from 1:100 to 1:1, preferably from 1:50 to 1:1.5, particularly preferably from 1:10 to 1:2.

The present invention further provides the intermediate of the method according to the invention, a solidified melt of a mixture comprising at least one wax and at least one ceramide. The wording clearly and unequivocally shows that by the abovementioned term, a solidified melt means that the at least one wax and at least one ceramide is the result of a previously melted mixture.

The solidified melt according to the invention of a mixture comprising at least one wax and at least one ceramide are preferably characterized in that, based on the total solidified melt, wax and ceramide are present therein in an amount of at least 80% by weight, preferably at least 90% by weight, particularly preferably at least 98% by weight.

In particular, the solidified melt according to the invention preferably comprise the ceramide, based on the total solidified melt, present in an amount of 2% by weight to 19% by weight, preferably 5% by weight to 18% by weight, particularly preferably 12% by weight to 17% by weight.

In accordance with the invention, preferred solidified melts are the preferred waxes and ceramides used in the preferred method according to the invention and also comprise preferred combinations of the two components.

The examples adduced hereinafter describe the present invention by way of example, without any intention that the invention, the scope of application of which is apparent from the entirety of the description and the claims, be restricted to the embodiments specified in the examples.

EXAMPLES

Example 1: Preparation of Solidified Melts Comprising Ceramide NP and Waxes 1 g of ceramide NP was heated, in each case together with 5 g of glyceryl stearate (TEGIN M® Pellets, Evonik Industries), stearic acid, polyglyceryl-3 dicitrate/stearate (TEGO® Care PSC 3, Evonik Industries) or cetearyl alcohol (TEGO® Alkanol 1618®, Evonik Industries), to 90° C. with stirring until a homogeneous liquid was formed. Subsequently, the mixture was allowed to cool to ambient temperature (ca. 20° C.), whereupon a solid mass was formed. This was comminuted into pellets.

Example 2: Lowering of Dissolution Temperature in Oils

The minimum required dissolution temperature for 0.1 g of ceramide NP in 20 g of various oils was determined.

The results are presented in Table 1 and show that the minimum required dissolution temperature can be significantly reduced when ceramide NP is solubilized in the form of a solidified, wax-containing melt.

TABLE 1

| | required dissolution temperatures in ° C. | | | |
|---|---|---|---|---|
| | Ceramide NP | Ceramide NP/ TEGIN ® M | Ceramide NP/ TEGO ® Alkanol 1618 | Ceramide NP/ Stearic Acid |
| *Persea gratissima* (Avocado) oil | 100 | 85 | 85 | 90 |
| Caprylic/Capric Triglycerides (TEGOSOFT ® CT) | 95 | 75-80 | 85 | 80 |
| Ethylhexyl Stearate (TEGOSOFT ® OS) | 100 | 85 | 85-90 | 85 |

Example 3: Lowering of Formulation Temperature in O/W Emulsions

The O/W face cream formulations of Table 2 were prepared as follows:

Phase A and B were heated separately to the specified temperatures, phase A added to phase B with stirring and homogenized. This was allowed to cool with gentle stirring.

TABLE 2

| Phase | Ingredient | w/w % CF1 | w/w % EF1 | w/w % EF2 |
|---|---|---|---|---|
| A | Polyglyceryl-3 Methylglucose Distearate (TEGO ® Care 450) | 3.0 | 3.0 | 3.0 |
| | Glyceryl Stearate (TEGIN ® M Pellets) | 2.0 | 1.5 | 2.0 |
| | Cetearyl Alcohol (TEGO ® Alkanol 1618) | 1.0 | 1.0 | 0.5 |
| | Caprylic/Capric Triglyceride (TEGOSOFT ® CT) | 6.0 | 6.0 | 6.0 |
| | Ethylhexyl Stearate (TEGOSOFT ® OS) | 5.0 | 5.0 | 5.0 |
| | Mineral Oil | 4.0 | 4.0 | 4.0 |
| | Ceramide NP | 0.1 | | |
| | Ceramide NP/TEGIN ® M pellets from Ex. 1 | | 0.6 | |
| | Ceramide NP/TEGO ® Alkanol 1618 from Ex. 1 | | | 0.6 |
| B | Glycerol | 3.0 | 3.0 | 3.0 |
| | Water | 75.9 | 75.9 | 75.9 |
| Z | Preservative, Perfume | q.s. | q.s. | q.s. |
| Required process temperature | | 90° C. | 75° C. | 75° C. |

Whereas the comparative formulation CF1 required a processing temperature of at least 90° C. in order to get the fully dissolved ceramide incorporated into the formulation, the same result is achieved even at 75° C. if ceramide NP is incorporated in the form of a solidified, wax-containing melt.

The skin repair cream formulations of Table 3 were prepared as follows:

Phase A and B were heated separately to the specified temperatures, phase A added to phase B with stirring and homogenized. The mixture was firstly allowed to cool to 60° C. with gentle stirring, phase C was then added, briefly homogenized, phase D added and the mixture further allowed to cool with gentle stirring.

TABLE 3

| Phase | Ingredients | w/w % CF2 | w/w % EF3 |
|---|---|---|---|
| A | Glyceryl Stearate (TEGIN ® 4100 Pellets) | 2.5 | 2.5 |
| | Stearyl Alcohol (TEGO ® Alkanol 18) | 1.5 | 1.5 |
| | Stearic Acid | 1.0 | |
| | Ceramide NP | 0.2 | |
| | Ceramide NP/Stearic Acid from Ex. 1 | | 1.2 |

TABLE 3-continued

| Phase | Ingredients | w/w % CF2 | w/w % EF3 |
|---|---|---|---|
| | Cetearyl Ethylhexanoate (TEGOSOFT ® liquid) | 9.8 | 9.8 |
| | Ethylhexyl Palmitate (TEGOSOFT ® OP) | 5.0 | 5.0 |
| | Caprylic/Capric Triglyceride (TEGOSOFT ® CT) | 3.0 | 3.0 |
| | Decyl Cocoate (TEGOSOFT ® DC) | 2.0 | 2.0 |
| B | Cetearyl Glucoside (TEGO ® Care CG 90) | 1.0 | 1.0 |
| | Glycerol | 3.0 | 3.0 |
| | Water | 70.5 | 70.5 |
| C | Carbomer (TEGO ® Carbomer 134) | 0.1 | 0.1 |
| | Cetearyl Ethylhexanoate (TEGOSOFT ® liquid) | 0.4 | 0.4 |
| D | Sodium Hydroxide (10% in water) | q.s. | q.s. |
| Z | Preservative, Perfume | q.s. | q.s. |
| | Required process temperature | 90° C. | 75° C. |

Whereas the comparative formulation CF2 required a processing temperature of at least 90° C. in order to get the fully dissolved ceramide incorporated into the formulation, the same result is achieved even at 75° C. if ceramide NP is incorporated in the form of a solidified, wax-containing melt.

The natural O/W lotion formulations of Table 4 were prepared as follows:

Phase A and B were heated separately to the specified temperatures, phase A added to phase B with stirring and homogenized. The mixture was firstly allowed to cool to 40° C. with gentle stirring, phase C was then added, briefly homogenized, phase D and phase E added, the pH adjusted to 5.2 and the mixture further allowed to cool with gentle stirring.

TABLE 4

| Phase | Ingredients | w/w % CF3 | w/w % EF4 |
|---|---|---|---|
| A | Polyglyceryl-3 Dicitrate/Stearate (TEGO ® Care PSC 3) | 3.0 | 2.0 |
| | Caprylic/Capric Triglyceride (TEGOSOFT ® CT) | 7.0 | 7.0 |
| | Isopropyl Palmitate (TEGOSOFT ® P) | 3.0 | 3.0 |
| | Cetyl Ricinoleate (TEGOSOFT ® CR) | 2.0 | 2.0 |
| | Persea Gratissima (Avocado) Oil | 5.0 | 5.0 |
| | Ceramide NP | 0.2 | |
| | Ceramide NP/TEGO ® Care PSC 3 from Ex. 1 | | 1.2 |
| B | Water | 75.1 | 75.1 |
| | Glycerol | 3.0 | 3.0 |
| C | Keltrol CG-SFT (Xanthan Gum) | 0.5 | 0.5 |
| D | Sodium Hydroxide (10%) | 0.2 | 0.2 |
| E | Rokonsal BSB-N | 1.0 | 1.0 |
| Z | Perfume | q.s. | q.s. |
| | Required process temperature | 90° C. | 75° C. |

Whereas the comparative formulation CF3 required a processing temperature of at least 90° C. in order to get the fully dissolved ceramide incorporated into the formulation, the same result is achieved even at 75° C. if ceramide NP is incorporated in the form of a solidified, wax-containing melt.

Example 4: One Pot Method

The O/W face cream formulations of Table 5 were prepared in the one-pot method as follows:

Water and glycerol were heated separately to the specified temperatures, the remaining ingredients were added gradually and homogenized keeping the temperature and stirring. This was allowed to cool with gentle stirring.

TABLE 5

| Phase | Ingredients | w/w % CF4 | w/w % EF5 |
|---|---|---|---|
| A | Water | 75.9 | 75.9 |
| | Glycerol | 3.0 | 3.0 |
| | Polyglyceryl-3 Methylglucose Distearate (TEGO ® Care 450) | 3.0 | 3.0 |
| | Glyceryl Stearate (TEGIN ® M Pellets) | 2.0 | 1.5 |
| | Cetearyl Alcohol (TEGO ® Alkanol 1618) | 1.0 | 1.0 |
| | Caprylic/Capric Triglyceride (TEGOSOFT ® CT) | 6.0 | 5.0 |
| | Ethylhexyl Stearate (TEGOSOFT ® OS) | 5.0 | 5.0 |
| | Mineral Oil | 4.0 | 4.0 |
| | Ceramide NP | 0.1 | |
| | Ceramide NP/TEGIN ® M from Ex. 1 | | 0.6 |
| | Preservative, perfume | q.s. | q.s. |
| | Required process temperature | 90° C. | 75° C. |
| | Comments: | Undissolved ceramide NP | Fully dissolved ceramide NP |

Whereas in the comparative formulation CF at a process temperature of 90° C. undissolved ceramide NP crystals are still present, by using ceramide NP in the form of a solidified wax-containing melt with TEGIN® M pellets, formulations are obtainable with fully dissolved ceramide even at a process temperature of 75° C.

A one-pot processing is only possible due to the solidified melt.

The invention claimed is:

1. A method for preparing a ceramide-containing formulation comprising the method steps of
   A) melting a mixture comprising a wax and a ceramide,
   B) cooling the molten mixture to obtain a solidified melt comprising the wax and the ceramide, and
   C) incorporating the solidified melt into an oil-containing formulation,
   wherein the ratio by weight of the wax to the ceramide is from 50:1 to 1:1.

2. The method according to claim 1, wherein the wax is selected from the group consisting of natural waxes of plant or animal origin, mineral waxes, fats, fatty alcohols, fatty acids, fatty esters, ethers of fatty alcohols, esters of polyethylene oxide and fatty acids, ethers of polyethylene oxide and fatty alcohols and partial glycerol esters.

3. The method according to claim 1, wherein the ceramide is selected from the group comprising Ceramide NP, Ceramide AP, Ceramide EOP, Ceramide NDS, Ceramide ADS, Ceramide EODS, Ceramide NS, Ceramide AS, Ceramide EOS, Ceramide NH, Ceramide AH and Ceramide EOH.

4. The method according to claim 3, wherein the ratio by weight of the wax to the ceramide in method step A) is from 9:1 to 4:1.

5. The method according to claim 1, wherein the ratio by weight of the wax to the ceramide is from
   20:1 to 2:1.

6. The method according to claim 1, wherein the mixture in method step A) and the solidified melt in method step B), based on the total mixture and total melt respectively,
   comprise from 70% by weight to 100% by weight, of the wax and the ceramide.

7. The method according to claim 1, wherein the mixture in method step A) is melted at a temperature of 80° C. to 105° C.

8. The method according to claim 1, wherein the oil-containing formulation in method step C) is an emulsion and the method steps comprise
- C1) heating an oil phase comprising the solidified melt,
- C2) heating an aqueous phase
- C3) homogenizing the combined oil phase and aqueous phase with each other.

9. The method according to claim 8, wherein in method step C1) and C2)
the phases are heated to a temperature of 60° C. to 89° C.

10. The method according to claim 8, wherein at least one oil and at least one emulsifier are present in the oil phase.

11. The method according to claim 8, wherein
the ratio by weight of oil phase to aqueous phase is from 1:100 to 1:1.

12. The method according to claim 8, wherein in method step C1) and C2)
the phases are heated to a temperature of 65° C. to 79° C.

13. The method according to claim 8, wherein
the ratio by weight of oil phase to aqueous phase is from 1:50 to 1:1.5.

14. The method according to claim 1, wherein the ratio by weight of the wax to the ceramide is from 9:1 to 4:1.

15. The method according to claim 1, wherein the mixture in method step A) and the solidified melt in method step B), based on the total mixture and total melt respectively, comprise from 81% by weight to 99% by weight of the wax and the ceramide.

16. The method according to claim 1, wherein the mixture in method step A) is melted at a temperature of 85° C. to 99° C.

17. The method according to claim 1, wherein the mixture in method step A) and the solidified melt in method step B), based on the total mixture and total melt respectively, comprise from 95% by weight to 98% by weight of the wax and the ceramide.

\* \* \* \* \*

UNITED STATES PATENT AND TRADEMARK OFFICE
CERTIFICATE OF CORRECTION

PATENT NO. : 11,000,458 B2
APPLICATION NO. : 16/491685
DATED : May 11, 2021
INVENTOR(S) : Ursula Maczkiewitz, Maria Mecking and Annika Schrader Page 1 of 1

It is certified that error appears in the above-identified patent and that said Letters Patent is hereby corrected as shown below:

Column 8,
Line 58, Claim 4, "the ceramide in method step A) is from" should read -- the ceramide is from --.

Signed and Sealed this
Eighth Day of June, 2021

Drew Hirshfeld
*Performing the Functions and Duties of the
Under Secretary of Commerce for Intellectual Property and
Director of the United States Patent and Trademark Office*